United States Patent
Remmlinger et al.

(10) Patent No.: US 6,895,808 B2
(45) Date of Patent: May 24, 2005

(54) METHOD AND DEVICE FOR MACHINE DIAGNOSIS, ESPECIALLY FOR TRANSMISSION DIAGNOSIS

(75) Inventors: Hubert Remmlinger, Friedrichshafen (DE); Robert Ingenbleek, Kressbronn (DE); Gabriele Schuwerk, Ravensburg (DE); Rolf Schmitz, Friedrichshafen (DE)

(73) Assignee: ZF Friedrichshafen AG, Friedrichshafen (DE)

( * ) Notice: Subject to any disclaimer, the term of this patent is extended or adjusted under 35 U.S.C. 154(b) by 0 days.

(21) Appl. No.: 10/613,676

(22) Filed: Jul. 3, 2003

(65) Prior Publication Data
US 2004/0050147 A1 Mar. 18, 2004

(30) Foreign Application Priority Data
Jul. 9, 2002 (DE) .......................................... 102 30 759

(51) Int. Cl.$^7$ ........................ G01M 13/00; G01N 27/74
(52) U.S. Cl. .................... 73/53.07; 73/61.42; 73/61.71; 324/204
(58) Field of Search .............................. 73/53.01, 53.05, 73/53.07, 61.42, 61.71; 324/204

(56) References Cited
U.S. PATENT DOCUMENTS
4,219,805 A 8/1980 Magee et al. ............... 340/631
5,594,173 A 1/1997 Frey et al.
6,435,013 B1 * 8/2002 Rodriguez et al. ......... 73/61.75

FOREIGN PATENT DOCUMENTS
DE    29 33 822 C2    10/1986
DE    44 29 311 C2    5/1998
DE    100 58 844 A1    6/2002
GB    2 029 580 A    3/1980 .......... G01N/27/72

* cited by examiner

Primary Examiner—Daniel S. Larkin
(74) Attorney, Agent, or Firm—Davis & Bujold, P.L.L.C.

(57) ABSTRACT

The present invention concerns a method and a device for machine diagnosis and, in particular, for transmission diagnosis in a machine or motor vehicle. The measurement system, according to the invention, comprises a coil (2) wound on a coil core (11), on the surface of which ferritic wear particles (3) to be detected accumulate. Opposite the coil (2) a rotating toothed wheel (6) is arranged which influences the inductance of the coil (2). The output signal of the coil (2) is pulsed with a constant amplitude, the pulse frequency depends on the rotation speed of the toothed wheel (6). Deviations of the amplitude are attributable to the accumulation of ferritic wear particles (3) on the coil (2) and therefore provide a measurement of the condition of the machine or transmission.

5 Claims, 1 Drawing Sheet

METHOD AND DEVICE FOR MACHINE DIAGNOSIS, ESPECIALLY FOR TRANSMISSION DIAGNOSIS

Figure 1:
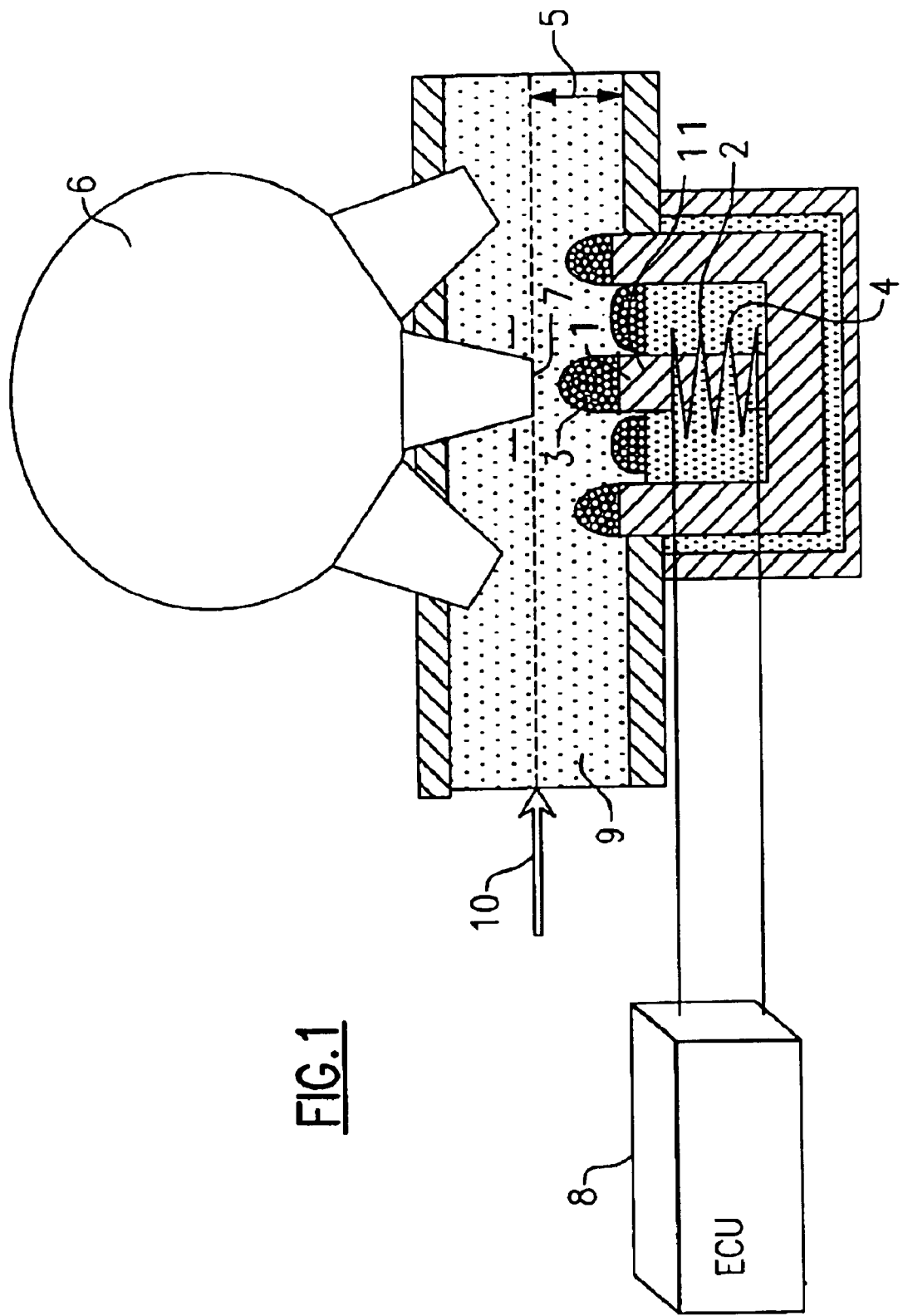

The present invention concerns a method for machine diagnosis and, in particular, for transmission diagnosis, of a machine or motor vehicle, according to the preamble of claim 1. In addition the invention concerns a device for implementing the method.

In modern machines and vehicle transmissions it is nowadays sought to fill these with engine oil and transmission oil once during their lifetime, and the life of such a transmission being, for example, typically on the order of 1 million kilometres.

The machine or transmission oil serves to lubricate and cool all the mechanical elements. Since it is never changed, it is exceptionally suitable for machine or transmission diagnosis since, over the course of time, all kinds of abrasion particles accumulate in the oil. Consequently, analysis of the machine or transmission oil provides information about the condition of the machine or transmission.

In this, ferritic wear is of particularly great importance since in almost any type of incipient damage, such as roller bearing wear, the formation of pitting in the gear teeth leading to tooth fracture, wear of the gear cage bolts, etc., ferritic wear alone, or in combination with other types of wear (non-ferrous metal wear, molybdenum degeneration, etc.), occurs.

In the state of the prior art there now exists an oil diagnosis system, disclosed by the present applicant in DE 100 58 844 A1, which detects ferritic wear metal by means of an inductive measurement system. This measurement system is incorporated in an oil duct of a transmission or machine. It uses a primary and a secondary coil, each wound around a magnetically soft core, and which are arranged on opposite sides of the oil duct. The coil arrangement forms a transformer whose iron circuit is divided between the two coils. A voltage applied to the primary coil produces a magnetic flux, which produces a back-induction voltage in the secondary coil. The level of this back-induction voltage depends on the coupling factor of the two coil which, in turn, depends on the accumulation of ferritic wear particles on the divided iron circuit. Accordingly, a change in back-induction voltage can be used as a measurement of the concentration of ferritic wear particles in the transmission oil.

Owing to its complexity and expensive components, an oil diagnosis system of this type proves to be costly. This feature, however, makes such developments uninteresting in the context of free competition. It is, therefore, necessary to continue seeking simple and inexpensive solutions.

Accordingly, the purpose of the present invention, starting from the prior art mentioned above, is to provide a method for machine diagnosis, and especially for transmission diagnosis, which selectively detects ferritic wear particles and enables simple and inexpensive on-line diagnosis of the condition of the machine or transmission.

This objective is achieved by the characteristics defined in the independent claim 1. Other advantageous features are indicated in the dependent claims.

The measurement system is located in the hydraulic circuit inside a transmission. It consists of a coil wound around a magnetically soft coil core and an electronic unit for the evaluation of the coil voltage and the coil inductance. The coil is located in an oil duct, for example, on the lower side thereof. Opposite the coil is a rotating toothed wheel. The pole surfaces of the toothed wheel fulfil the function of a signal emitter which influences the inductance, and hence also the voltage signal, of the coil.

The coil is inside a housing. Hollow spaces between the coil core and the housing are filled with a filling compound, while additional space is provided for the ferritic wear particles since the magnetically soft coil core projects above the height of the filling compound. This produces an annular recess. The projecting coil core acts as a pole surface on which the ferritic wear particles accumulate, for the most part. The distance between the pole surfaces of the coil and the toothed wheel, or gap size, is a constant value $h_0$.

The voltage signal from the coil is fed to an electronic control unit (ECU), which calculates the coil's inductance. The change in the voltage signal and the coil's inductance is used as a measure of the accumulated ferritic wear particles. In this way, ferritic wear particles present in the transmission oil are detected. This provides an early warning of wear in gear-wheels, bearings and other mechanically stressed components of the transmission. Total breakdown of the transmission is avoided and the high costs entailed by purchasing a new transmission unit can be reduced by carrying out repairs while still possible.

Other advantages of the invention are the following:

- the way in which the measurement system functions does not depend on the transport fluid;
- the way in which the measurement system functions does not depend on the cross-section of the duct;
- the way in which the measurement system functions is largely independent of the Reynolds number of the transport fluid and of air inclusions in it;
- the measurement method is characterized by effectiveness and robust construction; and
- the measurement system offers the possibility of on-line diagnosis.

Owing to the accumulation of ferritic wear particles, the magnetic flux in the coil changes which, in turn, brings about a change of the induced voltage in the coil. From the voltage and inductance characteristics, a conclusion about the accumulated ferritic wear particles can be drawn. The voltage or inductance characteristics can be evaluated, for example, by establishing a threshold value of the analog voltage signal. The definition of a threshold value for the analog signal depends on the measurement principle used. By virtue of the continued accumulation of ferritic wear particles over the total operation time of a transmission oil, an accumulation signal can be evaluated in which both an absolute value and its slope can be used.

For example, if the absolute value is exceeded, a datum is generated which signals the need to check or for maintenance of the transmission. In contrast, to consider the slope or gradient of the voltage or inductance characteristics, the gradients are compared with one another as a function of time and/or the running performance of the transmission. If the gradient changes to an excessive extent, in this case too a datum is also generated which serves as a warning of incipient transmission damage.

Alternatively, the signal can be considered in a time interval following a previous "Reset" operation. The reset takes place when the current of the electromagnet is turned off, so that the accumulated wear particles are released. Thereafter, the accumulation of ferritic wear particles can be measured afresh until a threshold voltage is reached and/or within a fixed time interval. This method increases the sensitivity of the sensor.

Moreover, the intermediate results of a number of previous measurements can be stored in a non-volatile memory, whose values enable statistical processing or averaging and evaluation of a chronological sequence.

Thus, various methods for evaluating the measurement signal can be imagined, which can be implemented with this type of sensor.

A particularly advantageous embodiment of the invention is the use of an already present revolution speed sensor modified in such a way that the ferritic wear particles accumulate on the pole surfaces of the coil.

This example embodiment has the advantage that costs are reduced because ultimately an already present sensor is additionally provided with the features required by the invention. Another advantage is the saving of space and weight achieved by using a single sensor for several applications.

Further advantages emerge from the example embodiment illustrated in the FIGURE.

The FIGURE is a schematic representation of the structure and functional mode of the measurement system according to the invention.

It shows a longitudinal section through part of an oil duct 9 of a transmission. The duct can have any cross-section. This does not compromise the function of the measurement system. The oil stream 10 flowing in the duct 9 is contaminated with ferromagnetic particles 3, mainly iron or steel particles. The local distribution of these particles is immaterial for the function of the measurement system, since the measurement system exerts an adjustable capturing action on the particles. The capturing action stems from an energized coil 2 which is wound round a soft magnetic core 11. The energized coil 2 acts as a permanent magnet, which filters the ferritic wear particles 3 out of the oil stream. The capturing effect is adjusted by the number N of turns on the coil 2, the materials used and the size of the electric current flowing through the coil 2. Thanks to the possibility of adjusting these parameters, the measurement system can be adapted for differing environmental conditions (duct cross-section, level of contamination and oil flow rate).

The coil 2 is positioned on the lower side of the oil duct 9. A rotating toothed wheel 6 is arranged opposite the coil 2. The distance or gap height between the pole surfaces of the coil core 11 and the tooth 7 is a constant value $h_0$. The inductance of the coil 2 is influenced by the toothed wheel 6 opposite it. When a tooth is directly over the coil 2, the measurement system experiences a maximum change in the voltage signal of the coil. Due to rotation of the toothed wheel 6, the voltage signal of the coil 2 varies as a series of pulses. In this way, by counting the pulses, the speed of the toothed wheel 6 can be determined. If ferritic wear particles 3 accumulate on the pole surfaces of the coil core because of its magnetic capturing action, the inductance of the coil 2 is also changed. This change is detected and evaluated by the electronic unit ECU 8. The change of the voltage signal from the coil 2, due to ferritic wear particles 3, can be determined by computation because the constant, pulsed variations produced by the rotation movement of the toothed wheel 6, can be construed as a type of "offset". Deviation from the "offset" is attributable to the accumulation of ferritic wear particles 3 and is, therefore, suitable for use as a measurement of the accumulated ferritic wear particles 3. In this way, ferritic wear particles 3 in the transmission oil can be filtered out and detected, and this serves as an early warning of incipient transmission damage.

REFERENCE NUMBERS

1 Pole surface of the coil core
2 Coil
3 Ferritic wear particles
4 Filling compound
5 Gap height $h_0$
6 Toothed wheel
7 Pole surface of toothed wheel
8 Electronic unit ECU
9 Oil duct
10 Oil stream
11 Coil core

What is claimed is:

1. A method of diagnosing a machine by detecting ferritic wear particles (3) deposited within oil circulating within the machine, the method comprising the step of:

detecting accumulation of the ferritic wear particles (3) deposited within the oil, circulating within the machine, by a measurement system having a coil (2); and generating an output signal from the measurement system which is indicative of a ferritic wear particle condition of the machine; and locating the coil (2) in a lower region of an oil duct (9) of the machine and influencing an inductance of the coil (2) by an element situated opposite the coil (2).

2. The method according to claim 1, further comprising the step of situating a toothed wheel (6) opposite the coil (2).

3. The method according to claim 1, further comprising the steps of locating an element opposite to the coil (2), and determining, with the measurement system, a rotation speed of the element located opposite the coil (2).

4. A device for diagnosis of a machine by analyzing oil circulating within the machine to detect ferritic wear particles located therein, wherein the device for diagnosis comprises:

a coil core (11) which is located in a lower region of an oil duct (9) with a coil (2) wound around the coil core (11);

a device for providing a measurement condition of the machine being coupled to the coil (2) for receiving an inductance signal therefrom influenced by accumulation of ferritic wear particles (3) adjacent the coil (2), whereby, during operation of the device for diagnosis of the transmission, the ferritic wear particles (3) to be detected accumulate on a surface of the coil (2) and influence the inductance of the coil (2), and hence the output signal therefrom, detected by the device for providing the measurement condition of the machine;

the device for providing the measurement condition of the machine being coupled to an indicator for indicating required servicing of the machine; and an element is arranged opposite to the coil (2) such that a voltage signal of the coil (2) is pulsed according to a rotation speed of the element arranged opposite to the coil (2).

5. The device according to claim 4, wherein the measurement system comprises an electronic unit (8) which detects an output signal from the coil (2) having at least two data:

first datum varying, in a pulsed way, from a constant amplitude, and second datum in a form of a deviation of the amplitude, where the deviation of the amplitude is attributable to accumulation of the ferritic wear particles (3) and a rotation speed of an element, arranged opposite the coil (2), is calculated from detected pulses.

* * * * *